US012799010B2

(12) United States Patent
Ioka

(10) Patent No.: US 12,799,010 B2
(45) Date of Patent: Nov. 17, 2026

(54) METHOD FOR BIOLOGICALLY TREATING PERSISTENT ORGANIC WASTE WATER CONTAINING OIL COMPONENT INCLUDING HIGHER FATTY ACID AND THICKENING POLYSACCHARIDE

(71) Applicant: SUIWA CO., LTD., Himeji (JP)

(72) Inventor: Nobusuke Ioka, Himeji (JP)

(73) Assignee: SUIWA CO., LTD., Himeji (JP)

( * ) Notice: Subject to any disclaimer, the term of this patent is extended or adjusted under 35 U.S.C. 154(b) by 293 days.

(21) Appl. No.: 18/837,157

(22) PCT Filed: Jun. 27, 2022

(86) PCT No.: PCT/JP2022/025494
§ 371 (c)(1),
(2) Date: Aug. 8, 2024

(87) PCT Pub. No.: WO2024/003978
PCT Pub. Date: Jan. 4, 2024

(65) Prior Publication Data
US 2025/0136489 A1 May 1, 2025

(51) Int. Cl.
*C02F 9/00* (2023.01)
*B01D 17/04* (2006.01)
(Continued)

(52) U.S. Cl.
CPC .............. *C02F 9/00* (2013.01); *B01D 17/047* (2013.01); *C12N 1/16* (2013.01); *C12N 1/20* (2013.01);
(Continued)

(58) Field of Classification Search
CPC .... C02F 9/00; C02F 1/682; C02F 3/12; C02F 3/28; C02F 3/343; C02F 3/347;
(Continued)

(56) References Cited

FOREIGN PATENT DOCUMENTS

| | | |
|---|---|---|
| JP | 4-235799 A | 8/1992 |
| JP | 2006-095377 A | 4/2006 |

(Continued)

*Primary Examiner* — Waqaas Ali
(74) *Attorney, Agent, or Firm* — Maschoff Brennan

(57) ABSTRACT

A method for biotreating persistent organic waste water containing a higher fatty acid and a thickening polysaccharide without adding chemicals includes subjecting waste water to an oil-water separating process to separate it into aerobically treatable oil-containing waste water and anaerobically treatable polysaccharide-containing waste water. The anaerobically treatable polysaccharide-containing waste water is subjected to a reducing process in an anaerobic treatment to convert the polysaccharide in the waste water into a monosaccharide and to obtain monosaccharide water capable of aerobic treatment. The oil-containing waste water and the monosaccharide containing water are subjected to an aerobic bacteria treatment process to yield pretreatment water capable of aeration treatment. The pretreatment water is subjected to an aeration treatment process while controlling BOD density and is subjected to a solid-liquid separation by flocculating with activated sludge.

5 Claims, 11 Drawing Sheets

All processing flow

(51) Int. Cl.

| | |
|---|---|
| ***C12N 1/16*** | (2006.01) |
| ***C12N 1/20*** | (2006.01) |
| *C02F 1/68* | (2023.01) |
| *C02F 3/12* | (2023.01) |
| *C02F 3/28* | (2023.01) |
| *C02F 3/34* | (2023.01) |
| *C02F 101/32* | (2006.01) |
| *C02F 101/34* | (2006.01) |

(52) U.S. Cl.

CPC ................ *C02F 1/682* (2013.01); *C02F 3/12* (2013.01); *C02F 3/28* (2013.01); *C02F 3/343* (2013.01); *C02F 3/347* (2013.01); *C02F 2101/32* (2013.01); *C02F 2101/34* (2013.01); *C02F 2209/08* (2013.01)

(58) Field of Classification Search

CPC .............. C02F 2101/32; C02F 2101/34; C02F 2209/08; C02F 1/24; C02F 1/40; C02F 3/34; B01D 17/047; C12N 1/16; C12N 1/20; Y02W 10/10

See application file for complete search history.

(56) References Cited

FOREIGN PATENT DOCUMENTS

| | | | | | |
|---|---|---|---|---|---|
| JP | 2011-31206 | A | | 2/2011 | |
| JP | 2011031206 | A | * | 2/2011 | |
| JP | 2019-214039 | A | | 12/2019 | |
| JP | 2020-104116 | A | | 7/2020 | |
| WO | WO-2012046476 | A1 | * | 4/2012 | ................ C02F 3/28 |
| WO | 2013/137010 | A1 | | 9/2013 | |

* cited by examiner

3rd process: Aerobic biological pretreatment process flow

4th process: Flow of the exposure and solid-liquid separation process

Overview diagram of all facilities

Oil separation equipment overview

Diagram of reduced polysaccharide synthesis

Aeration and solid-liquid separation process equipment overview

METHOD FOR BIOLOGICALLY TREATING PERSISTENT ORGANIC WASTE WATER CONTAINING OIL COMPONENT INCLUDING HIGHER FATTY ACID AND THICKENING POLYSACCHARIDE

FIELD OF THE INVENTION

The present invention relates to a method for perfect biological treatment of wastewater in an activated sludge process, and more particularly, to an improved biological treatment of an activated sludge process in which a persistent organic waste water contains an oil component containing higher fatty acids and a thickening polysaccharide which has contradictory properties, without adding any coagulation chemical compound which is an obstacle to the activated sludge method.

BACKGROUND OF THE INVENTION

In recent years, the activated sludge method is widely used as a biological treatment method for waste water. The activated sludge method is an aerobic biological treatment in which a sludge containing aerobic bacteria and the like is artificially added, and the organic matter is oxidized and decomposed by an aeration blowing air for a long time, and then the sludge is flocked, separated by sedimentation, and removed from the water in order to purify the water.

Incidentally, in a recent year, there has been a tendency to use a large amount of the oil component at the time of food production, so that it is preferable to perform an aerobic treatment using a lipase enzyme after flotation treatment of the oil and fat component in the waste water, because the oil component tends to reduce the processing ability of the microorganism when the waste water contains a large amount of the oil and fat component. On the other hand, due to health, there have been many cases in which an indigestible or resistant dextrin or the like that is difficult to decompose in the body, such as a thickening polysaccharide is used in place of use of sugar. Therefore, in the case where a large amount of the resistant dextrin or the like is present in the waste water, there is a phenomenon in which the viscosity increases in the aerobic treatment, so that the solid-liquid separation in the activated sludge method becomes difficult. Therefore, although an anaerobic treatment method containing higher fatty acids is proposed in the wastewater containing the oil component, (Patent Documents 1 and 2), the process proceeds with the methane fermentation, so that it was found that, when in the anaerobic treatment, the higher fatty acids and the thickening polysaccharide are contained at the same time, the process cannot be performed successfully. The reason why the process cannot be performed successfully is that the biodegradation treatment of the thickened polysaccharide and the oil containing the higher fatty acid are contradictory each other, that is, while the aerobic treatment using the lipase enzyme is preferable for the oil content, the aerobic treatment is not preferable for the thickened polysaccharide because of generation of viscosity and the waste water containing the thickened polysaccharide is recommended to be treated by the anaerobic method. On the other hand, when the oil content is present in the wastewater, the oil content in the anaerobic treatment tends to coagulates, and then the biological treatment is inhibited, so that the wastewater containing the oil content is preferably treated by aerobic method.

Therefore, since it is difficult to perform biological treatment when both of the oil content and the thickened polysaccharide are present at the same time, it is necessary at present to perform coagulation separation by pretreatment coagulation chemicals. However, since a large amount of coagulated sludge is generated by using the coagulation chemicals, there happens a problem of treatment of this large industrial waste, because the running cost iincreases.

Therefore, in order to improve the efficiency of the activated sludge method, it is proposed that the persistent organic wastewater containing the higher fatty acid and the thickening polysaccharide at the same time should be treated with a microorganism without adding or introducing a chemical drug which is an obstacle to the activated sludge method.

PRIOR ART

Patent Document 1: JP-A-2006-95377

Patent Document 2: JP-A-2020-104116

SUMMARY OF THE INVENTION

Problem to be Solved by the Invention

An object of the present invention is to provide a method for efficiently biotreating a persistent organic wastewater containing an oil component containing higher fatty acids and a thickening polysaccharide (which are contradictory persistent organic components), without adding any chemical drugs which are an n obstacle to the activated sludge method.

Configuration for Solving the Problem

As a result of intensive research, the present inventors have found the following phenomenon. First, 1) it was found that the remaining polysaccharide-containing wastewater W2 became an anaerobically treatable wastewater when the oil content was successfully removed from the persistent organic wastewater W, even if the wastewater contains the oil content containing higher fatty acids and the thickening polysaccharide. On the other hand, secondly 2) although the presence of viscous polysaccharide in wastewater makes the effect of process worse, it was found that, when the residual polysaccharide in the wastewater W2 can be converted to monosaccharide, the wastewater W2 can be treated in the aerobic pretreatment step. Because the increase of viscosity would be caused by oxidation of the polysaccharide atomic by oxygen by the aerobic treatment, it would be caused by atomic oxygen in the aerobic treatment. In addition, thirdly 3) it was found that, when the persistent organic wastewater W containing higher fatty acid and thickening polysaccharide was separated into an oil-containing wastewater W1 and a polysaccharide-containing wastewater W2, and the polysaccharide in the wastewater W2 was changed to monosaccharide, both the wastewater W1 and W2 were aerobically treated by marine bacteria, and it became the proper wastewater for the aeration treatment by the activated sludge method. Finally, 4) it has been also found that, since the monosaccharide water W4 becomes reduced and neutralized by anaerobic biological treatment, it is preferable for adjusting BOD loading during activated sludge treatment.

As a result after integrating these findings, we found that, the difficult organic wastewater W containing thickening polysaccharides and higher fatty acids can be substantially perfect-biotreated in the whole organism treatment process.

The present invention has been made based on the above findings, and firstly, there is provided a method for biotreating persistent organic waste water W containing an oil component containing higher fatty acids and a thickening polysaccharide, comprising the steps of:

A) subjecting a waste water W to an oil-water separating process to separate it into an aerobically treatable oil-containing waste water W1 and an anaerobically treatable polysaccharide-containing waste water W2, B) subjecting the anaerobically treatable polysaccharide-containing waste water W2 to a reducing process to convert the polysaccharide in the waste water W2 into a monosaccharide and to obtain a monosaccharide water W4 capable of aerobic treatment, C) subjecting the oil-containing waste water W1 and the monosaccharide containing water W4 to an aerobic bacteria treatment process into a pretreatment water W5 capable of aeration treatment, D) subjecting the pretreatment water W5 capable of aeration treatment to an aeration treatment process while controlling BOD density, resulting in a solid-liquid separation by flocculating with activated sludge.

Further, the second aspect of the present invention is to provide an improvement of the oil-water separating step A) in the activated sludge method, wherein the oil-water separation is carried out by a pressurized flotation, and the oil-containing wastewater W1 having an oil content containing high-grade fat acids is subjected to an emulsification process by adding an oil dispersing agent in order to be an efficient aerobiotic water W3.

Further, the third aspect of the present disclosure is to provide an improvement in the reducing step B), wherein the polysaccharide-containing waste water W2 after separated from the oil-containing waste water W1, is subjected to a reducing treatment process by *Bacillus subtilis* or the like to convert the polysaccharide into the monosaccharide to be capable of aerobic pretreatment.

Further, the fourth aspect of the present invention is to provide an improvement in the pretreatment process C) wherein the waste water containing an oil-containing waste water W1 or the aerobic-treatable emulsified water W3 can be treated together with the monosaccharide containing water W4 capable of aerobic pretreatment by using one of marine bacteria including Tolla yeast to obtain a waste water W5 capable of being treated with activated sludge.

Finally, this invention is to provide an improvement in the aeration treatment D) of the pretreatment water W5, wherein the pretreatment water is appropriately loaded with the reduced neutralized water W4 in the activated sludge.

Effect of the Invention

According to the present invention, it is possible to substantially perform the entire process using a biological treatment without adding chemical injection which becomes an obstacle in the activated sludge method, even if the waste water contains an oil content containing higher fatty acids and a thickening polysaccharide, and thus the amount of industrial waste is significantly reduced. Therefore, this invention can be said an epoch-making one.

Further, according to the present invention, the activated sludge treatment can be efficiently performed, even if the waste water contains an oil content containing higher fatty acids and a thickening polysaccharide, because 1) the oil which is a hindrance during the anaerobic biological treatment, can be removed up to a state where the anaerobic treatment is possible and also 2) a thickening polysaccharide which is hindered in the aeration step of the subsequent activated sludge method, can be converted to the monosaccharide in a manner to prevent the thickening phenomenon in the subsequent activated sludge method, Further, according to the present disclosure, since the pressurized flotation method is used in the oil-water separation step A), the oil-containing waste water W1 containing a higher fatty acid can be received in an oil dispersing tank, and then the oil dispersing agent is introduced into the oil dispersing tank to form an emulsion, whereby it can be efficiently formed into aerobic bio-treatable water, so that the oil component is not necessary to be retreated as an industrial waste.

Furthermore, according to the present disclosure, although the oil and the polysaccharide which are difficult to be treated simultaneously, they are separated into an oil-containing waste water W1 and a polysaccharide-containing waste water W2, and the oil-containing waste water W1 is preferably emulsified so as to be capable of aerobic treatment, while the polysaccharide-containing waste water W2 is converted to the monosaccharide containing water W4 capable of the aerobic treatment, so that both wastewaters W2 and W4 can be bio-treated in the aerobic treatment.

Finally, since the reduced neutralized water W4 obtained in step B) which contains the monosaccharide, is suitable for controlling the effective loading in the activated sludge aeration step, it is easy to manage the activated sludge method in which the entire process can be performed by the biological treatment.

EMBODIMENT OF THE INVENTION

The invention will now be described by way of example with reference to the accompanying drawings.

The present invention is a method for biotreating wastewater W containing an oil component containing higher fatty acids and a thickening polysaccharide. In the present invention, the thickening polysaccharide refers to a polysaccharide that generates viscosity in an activated sludge process, and includes isomerized sugar, water, oligosaccharides, starch, agar (including gelling agents such as carrageenan or Furcelleran), pectin, alginic acid, tamarind gum, natural gums, gum syrup, persistent dextrin, and the like. On the other hand, the oil component includes higher fatty acids, fats and oils (triglycerides), and the like.

The whole organism treatment process of the present invention is as follows.

Figure 1:
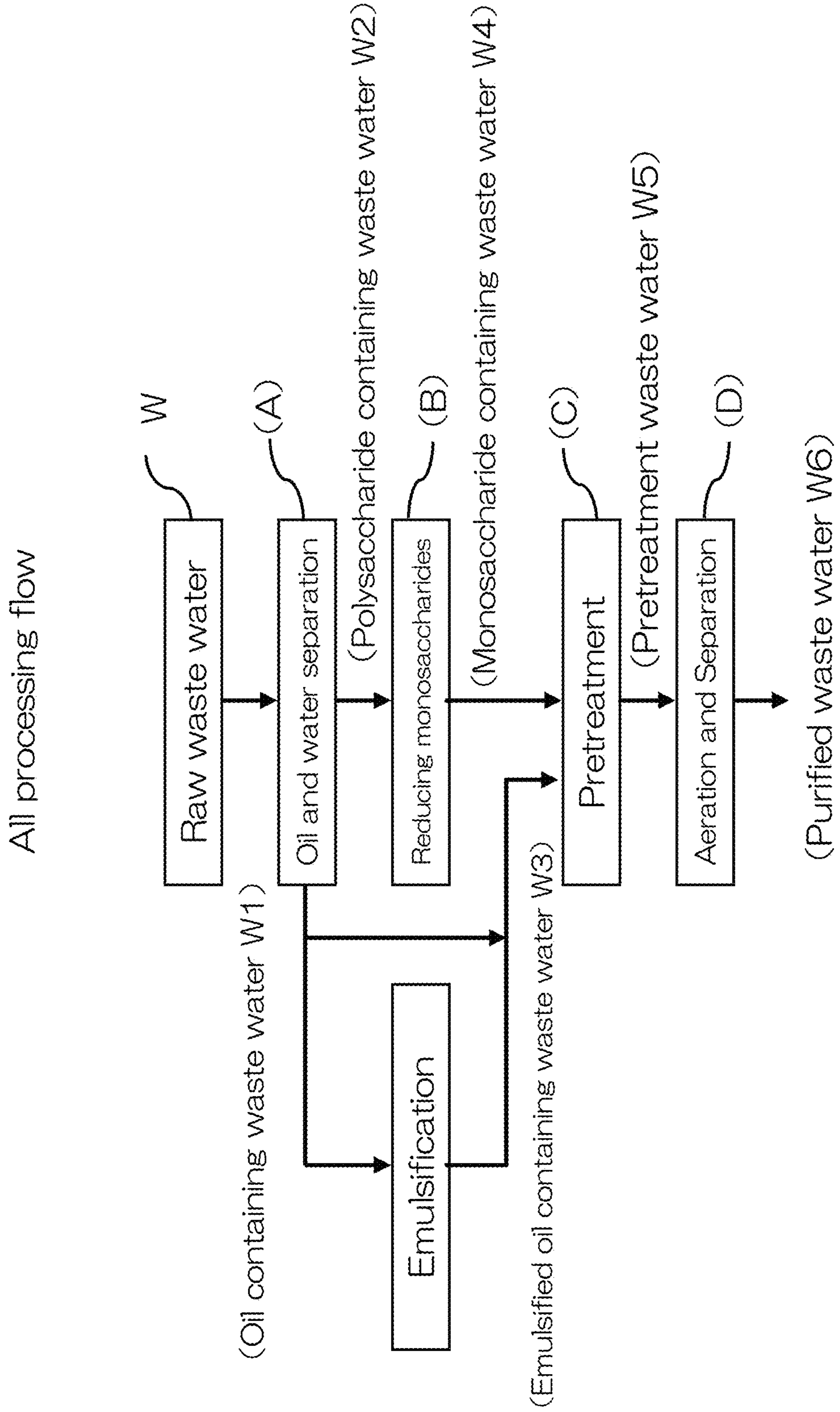
FIG. 1 it is a process flow diagram consisting of a total-stroke oil-water separation step A), a reducing monosaccharide step B), an aerobic pretreatment step C) and an aeration solid-liquid separation step D) of the method for treating wastewater according to the present invention.

As shown in FIG. 1, the waste water W is adjusted to a predetermined concentration, oil-water separation is performed in the first step (A), and the oil-containing waste water W1 and the polysaccharide-containing waste water W2 are separated. Then, the polysaccharide containing waste water W2 is sent to the reducing monosaccharide step (B), while the oil containing waste water W1 is sent directly to the pretreatment step (C), or is emulsified and sent to the pretreatment step (C). Here, the polysaccharide containing wastewater W2 is treated to monosaccharide wastewater W4 in the reduction monosaccharide process (B), and the monosaccharide containing wastewater W4 is sent to the pretreatment process (C). In the pretreatment step (C), the oil-containing waste water W1 is pretreated as it is or as an emulsified water W3 together with the monosaccharide-treated water W4. This pretreatment water W5 is aerated and separated into solid and liquid to form a purified waste water W6.

Therefore, in the present invention, there are provided A) a step of separating the waste water W into an aerobic oil-containing waste water W1 and an anaerobic polysaccharide-containing waste water W2 in which an oil component is separated, and B) a step of reducing a polysaccharide to monosaccharide treatment in the residual anaerobic polysaccharide containing waste water W2 in which the oil component is separated. The present method further comprises the step of (C) converting the oil-containing waste water W1 and the monosaccharide containing water W4 into a pretreatment water W5 capable of being aerated; and the step of (D) aerating the pretreatment water W5 capable of being aerated while controlling BOD content, flocking with activated sludge, and solid-liquid separation. Therefore, according to the present invention, the waste water W can be substantially treated using biological treatment even if the waste water contains an oil content containing higher fatty acids and a thickening polysaccharide.

Figure 2:
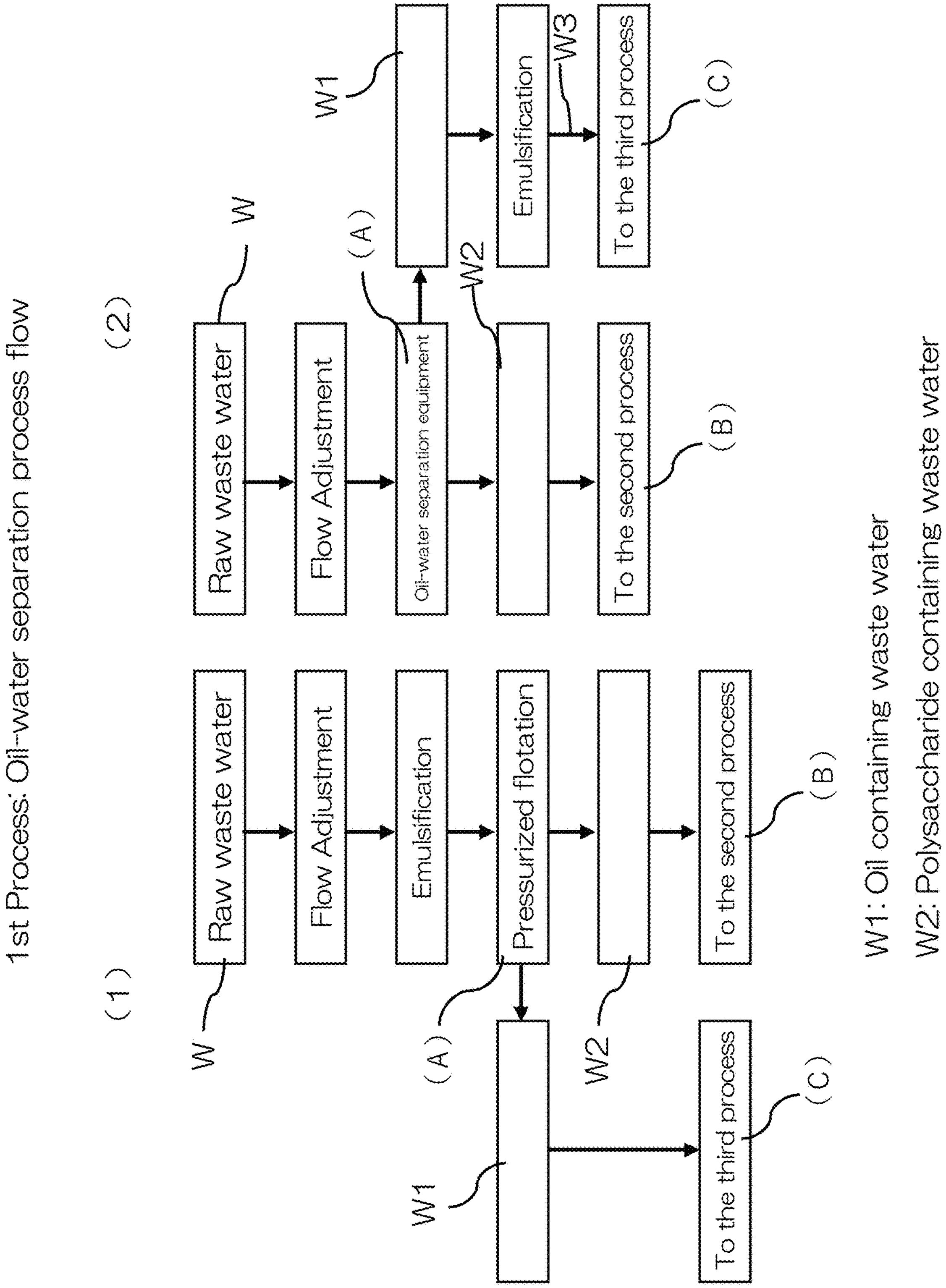
FIG. 2 it is a process flow diagram (1) and (2) showing an oil-water separation step A) of a first stroke of the wastewater treatment method of the present invention.

Specifically, in the first step (A) of the oil-water separation, as shown in FIG. 2, the raw waste water W is adjusted to a predetermined concentration (for example, n-hexane 500 ppm or less, BOD concentration 1500 to 3000 or less), adjusted to a predetermined flow rate, emulsified in the first step (1) and subjected to a chemical-free pressure flotation treatment, separated into an oil-containing waste water W1 and a polysaccharide-containing waste water W2, and the oil-containing waste water W1 is directly sent to the third step (C), while the polysaccharide-containing waste water W2 is sent to the second step (B). On the other hand, in another method (2) of the first step (A) the oil-containing waste water W1 and the polysaccharide-containing waste water W2 are separated in another oil-water separation step, and the oil-containing waste water W1 is emulsified and sent to the third step (C), while the polysaccharide-containing waste water W2 is sent to the second step (B).

Figure 3:
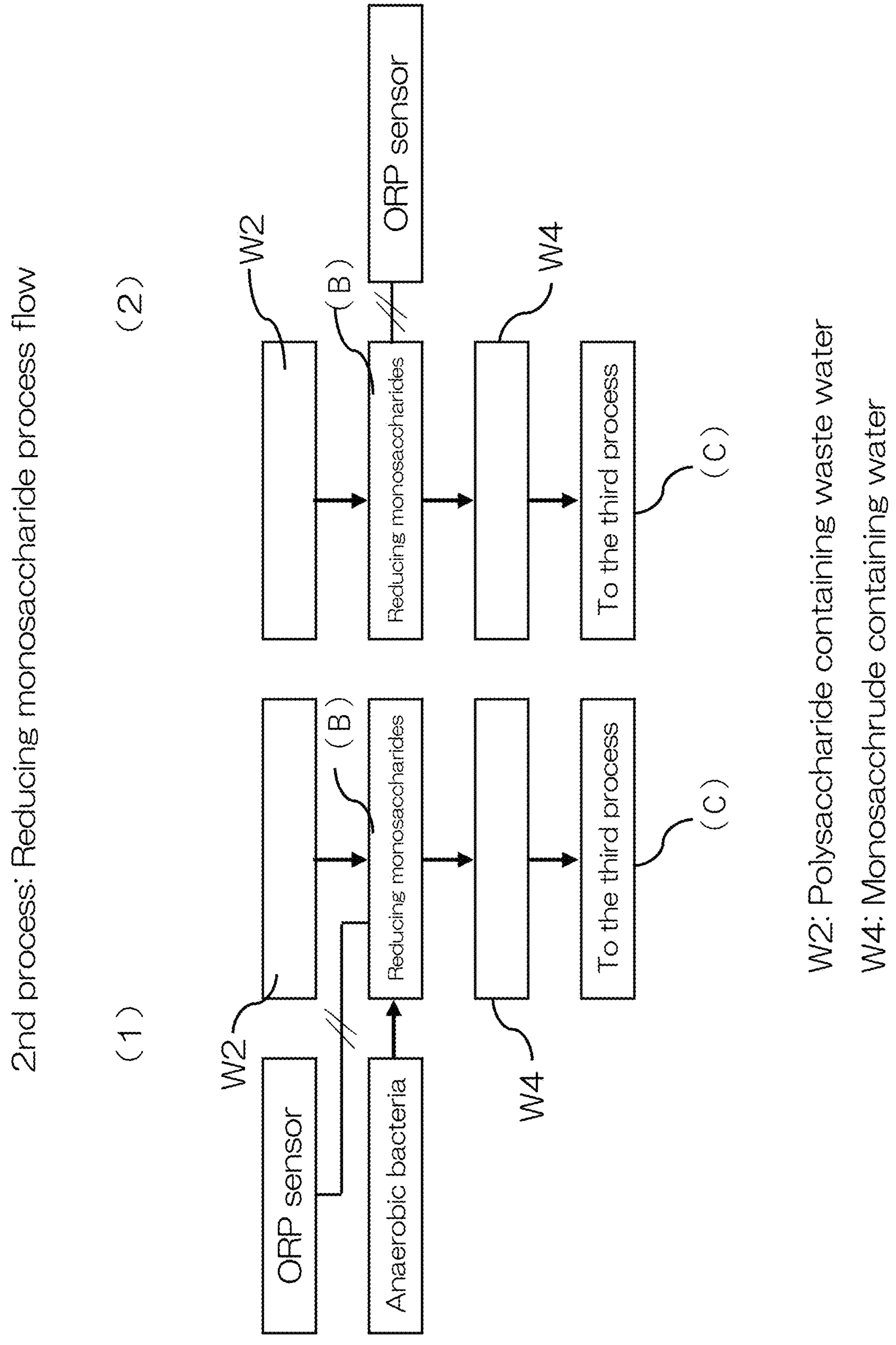
FIG. 3 it is a process flow diagram (1) and (2) showing a polysaccharide reducing monosaccharide step B) of the second process of the method for treating wastewater of the present invention.

Next, in the second step (B) of reducing the polysaccharide to the monosaccharide, as shown in FIG. 3, in (1) of the second step (B), the polysaccharide-containing waste water W2 is fed to the pretreatment step of the third step (C), where the polysaccharide-containing waste water W2 is treated by introducing an anaerobic bacterium (*Bacillus subtilis*) while measuring the oxidation-reduction potential by ORP sensor to become the monosaccharide containing waste water W4. On the other hand, in (2) of the second step (B), the polysaccharide-containing wastewater W2 is fed to the pretreatment step of the third step (C) by naturally introducing the anaerobic bacteria existing in the atmosphere while measuring the oxidation-reduction potential by ORP sensor to become the monosaccharide containing waste water W4. The former (1) is preferably applied when the reduction treatment tank is small, and the latter (2) is preferably applied when the reduction treatment tank is large.

Figure 4:
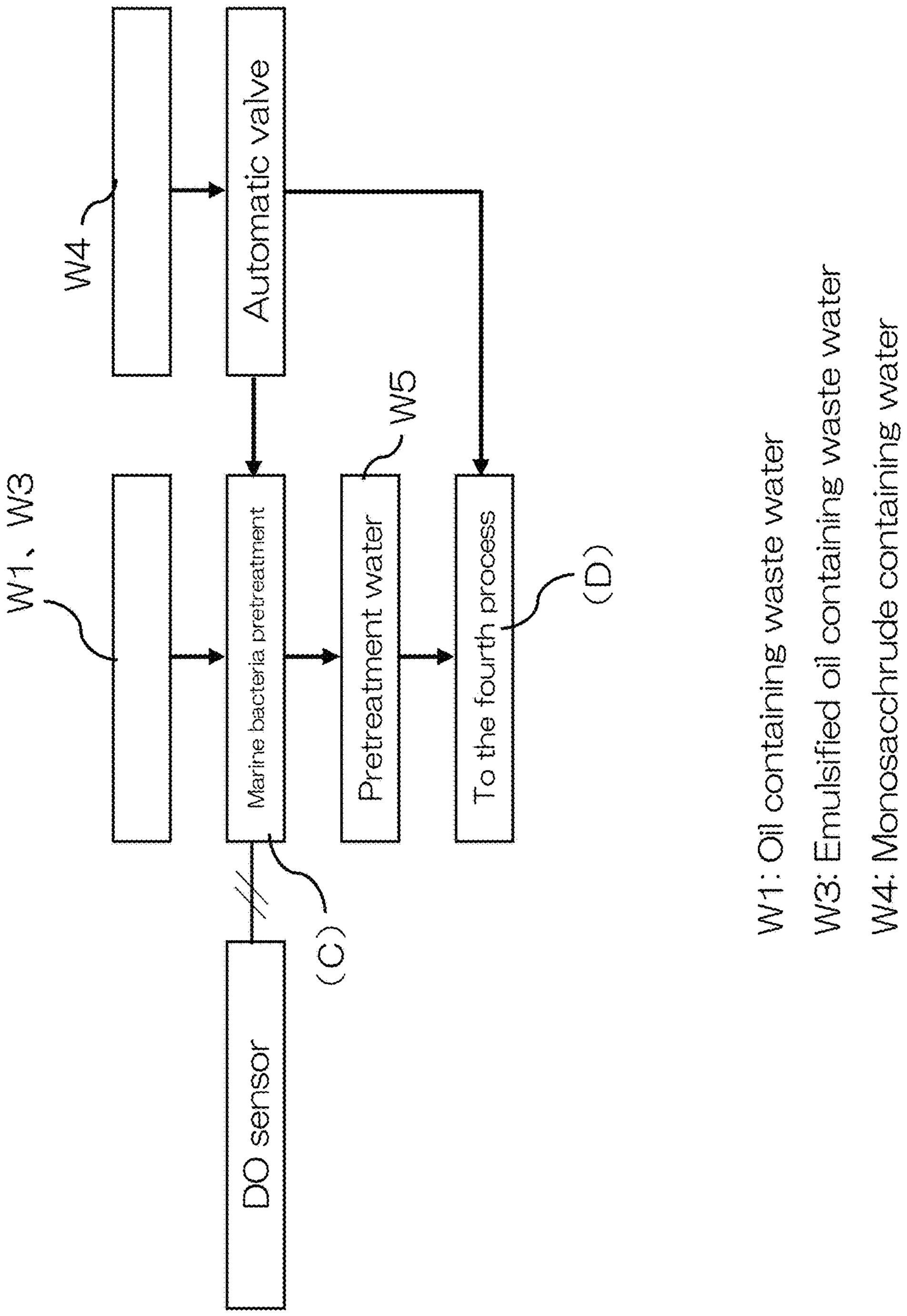
FIG. 4 it is a process flow diagram showing an aerobic organism pretreatment step C) of a third process of the wastewater treatment method of the present invention.

In the third step (C), as shown in FIG. 4, the oil-containing waste water W1 is preferably emulsified, but may be left as it is. Oil-containing wastewater W1 or emulsified oil-containing wastewater W3 are aerobically treated with marine bacteria, including Torula yeast. At this time, since the polysaccharide-containing waste water W2 separated by the oil-water separation (A) becomes the aerobic treatment possible water by the reducing polysaccharide to monosaccharide treatment (B), the oil-containing waste water W1 or the emulsified oil-containing waste water W3 and the monosaccharide containing water W4 are simultaneously aerobic pretreated to form an aerobic pretreatment water W5. This is sent to the activated sludge treatment step (D) which is the fourth step.

Figure 5:
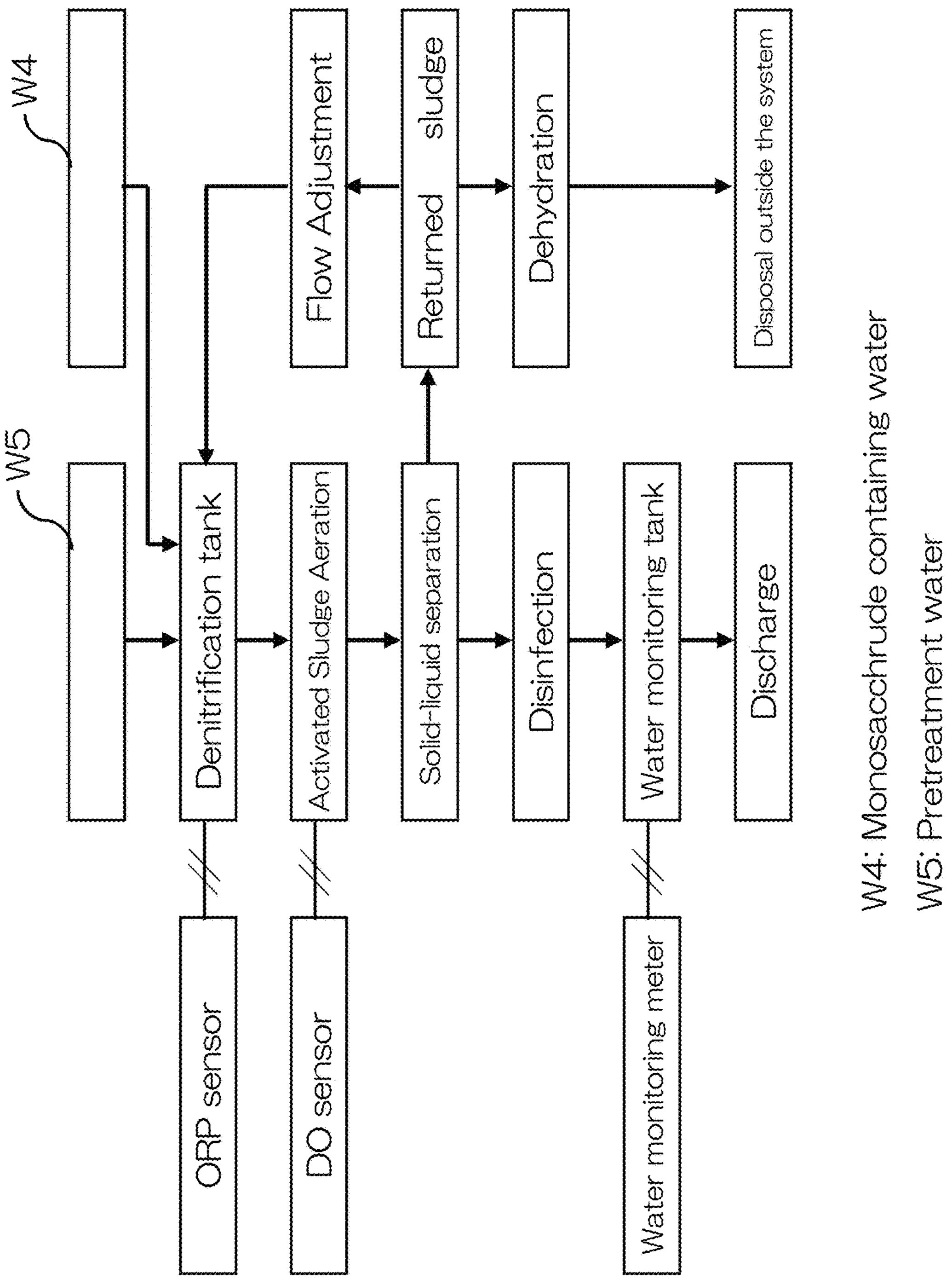
FIG. 5 it is a process flow diagram showing the the fourth aeration solid-liquid separation step D) of the wastewater treatment method of the present invention.

As shown in FIG. 5, an oxidation-reduction potential of aerobic pretreatment water W5 is measured by an ORP sensor in a denitrification tank, and is sent to a standard activated sludge treatment step (D) by adding a monosaccharide treatment water W4 to adjust the load to an appropriate load, and be performed by an aeration treatment while measuring an oxygen demand by a DO sensor, Then, an organic substance flocks, which results in a solid-liquid separation, and is sent to a discharge monitoring tank, and a purified water is discharged while monitoring the amount of stored water by a discharge water monitoring meter. A part of the sludge separated from the solid and liquid process is returned to the denitrification tank while the flow rate is adjusted, and the remainder is dehydrated to form a waste disposal.

FIG. 6 to FIG. 11 are facilities for carrying out the method of the invention described above.

1) (Preparation Step)

Figure 6:
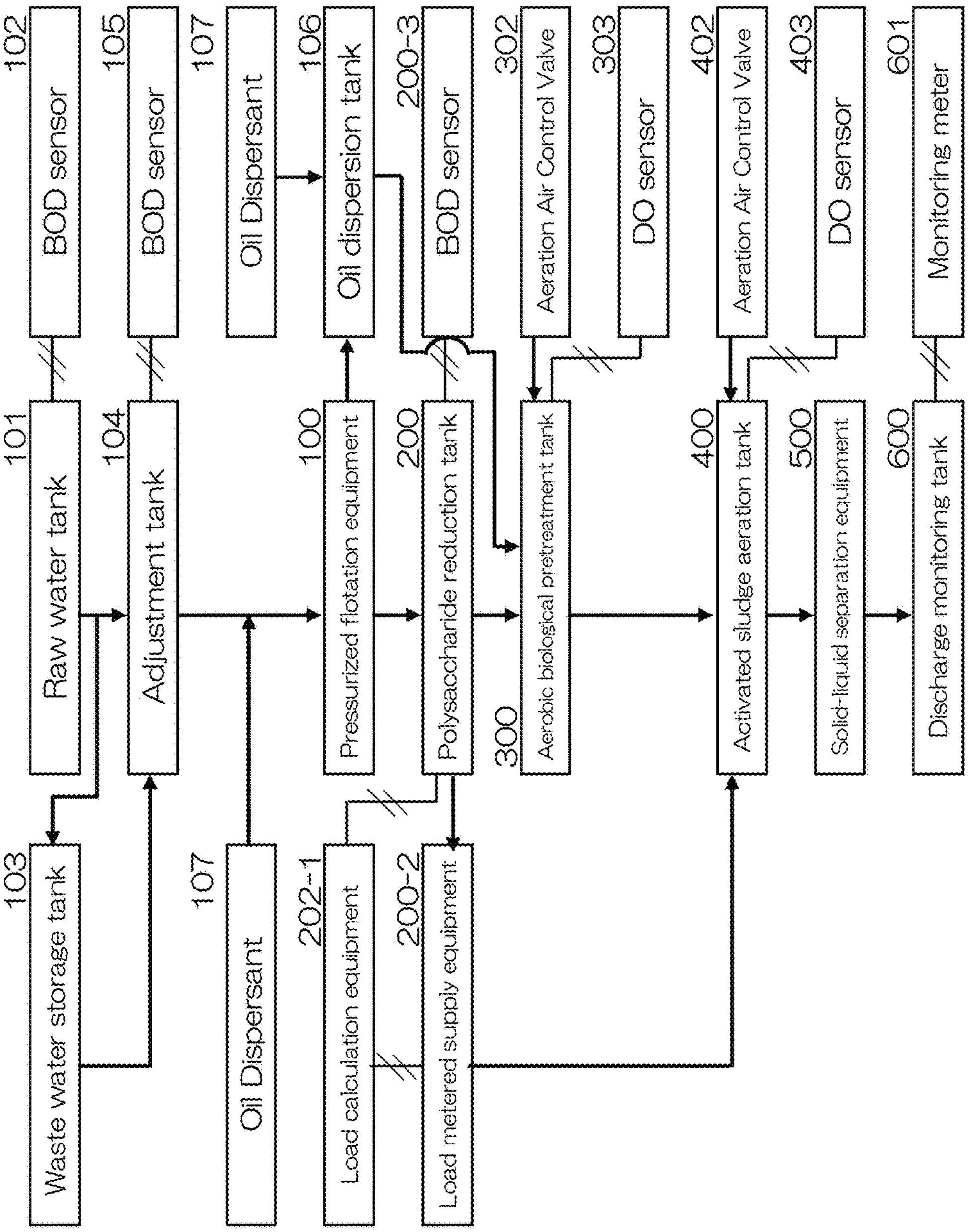
FIG. 6 it is a schematic diagram of an apparatus according to the present invention for carrying out an oil-water separation step A), a reducing monosaccharide step B), an aerobic pretreatment step C), and an aeration solid-liquid separation step D).

As shown in FIG. 6, the raw water such as industrial wastewater is stored in a raw water tank 101, and the organic matter level in the wastewater is measured by a first BOD sensor 102 including an absorbance sensor or the like. When BOD is high, a portion is stored in the high-concentration wastewater storage tank 103. When BOD concentration in the raw water is low, the high concentration wastewater is sent to the adjusting tank 104, and BOD concentration in the wastewater to be treated is measured by the second BOD sensor 105 and adjusted to a predetermined BOD concentration. When the wastewater should be purified in an actual treatment facility, the amount of wastewater flowing into the treatment facility is not constant, and may vary for some reason, and BOD level may vary for some reason even if the inflow amount of wastewater is constant. In such a case, the load on microorganisms (hereinafter referred to as the biological load) also varys, so that the operation of the equipment may become unstable. Therefore, the flow rate of the wastewater flowing into the raw water regulating tank is measured by a flow rate sensor, BOD density of the wastewater prior to flowing into the raw water regulating tank is measured by an absorbance sensor, the magnitude of the biological load is determined from the flow rate and BOD density of the wastewater, when the biological load exceeds the set value, it is preferable to feed the wastewater to a system other than the raw water regulating tank, it is possible to adopt the system described in our U.S. Pat. No. 4,097,505.

2) (Oil Content Pressurizing and Floating Step)

Figure 7:
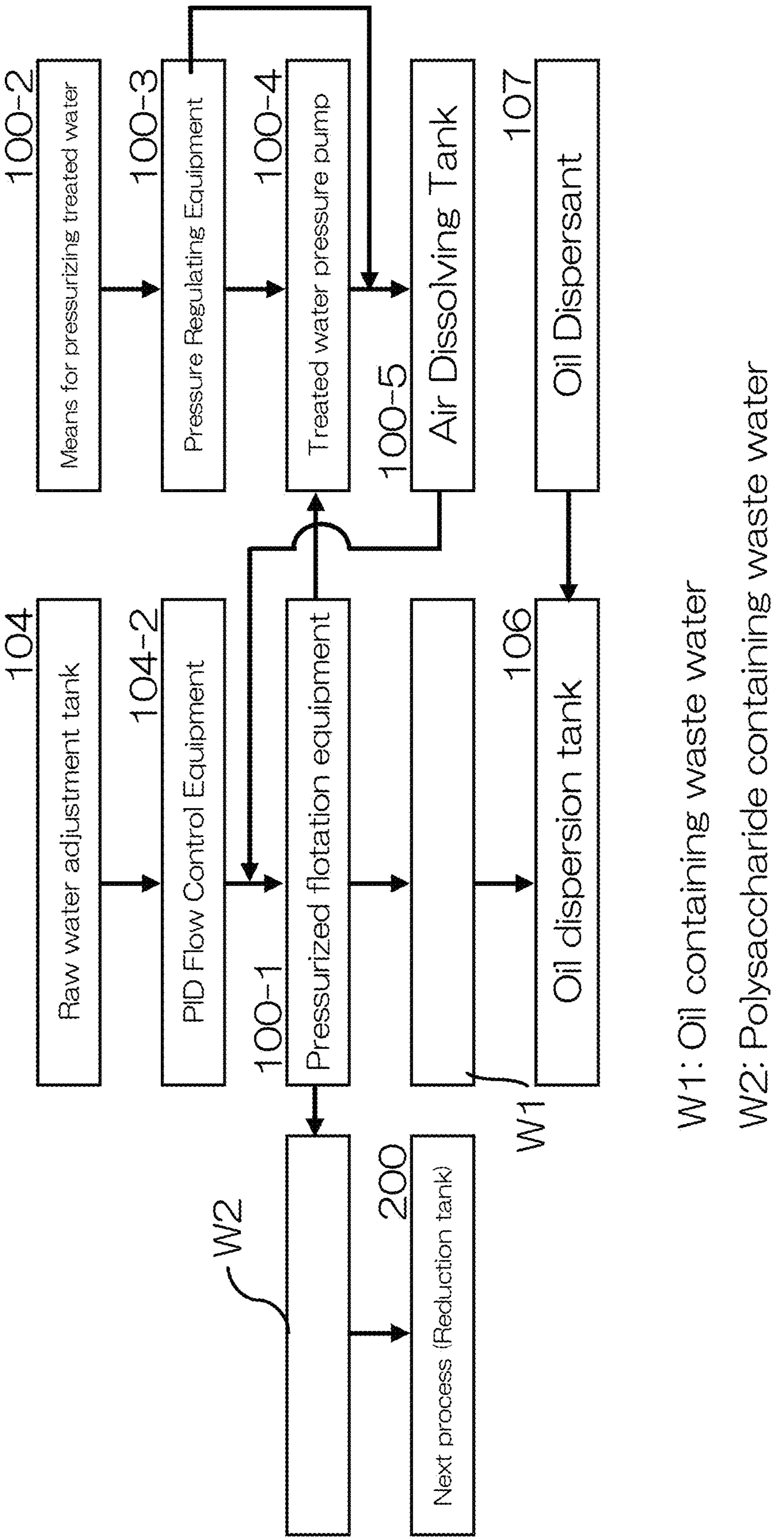
FIG. 7 it is a schematic view of a facility for carrying out the first oil-water separation step A) of the method for treating wastewater according to the present invention.
Figure 8:
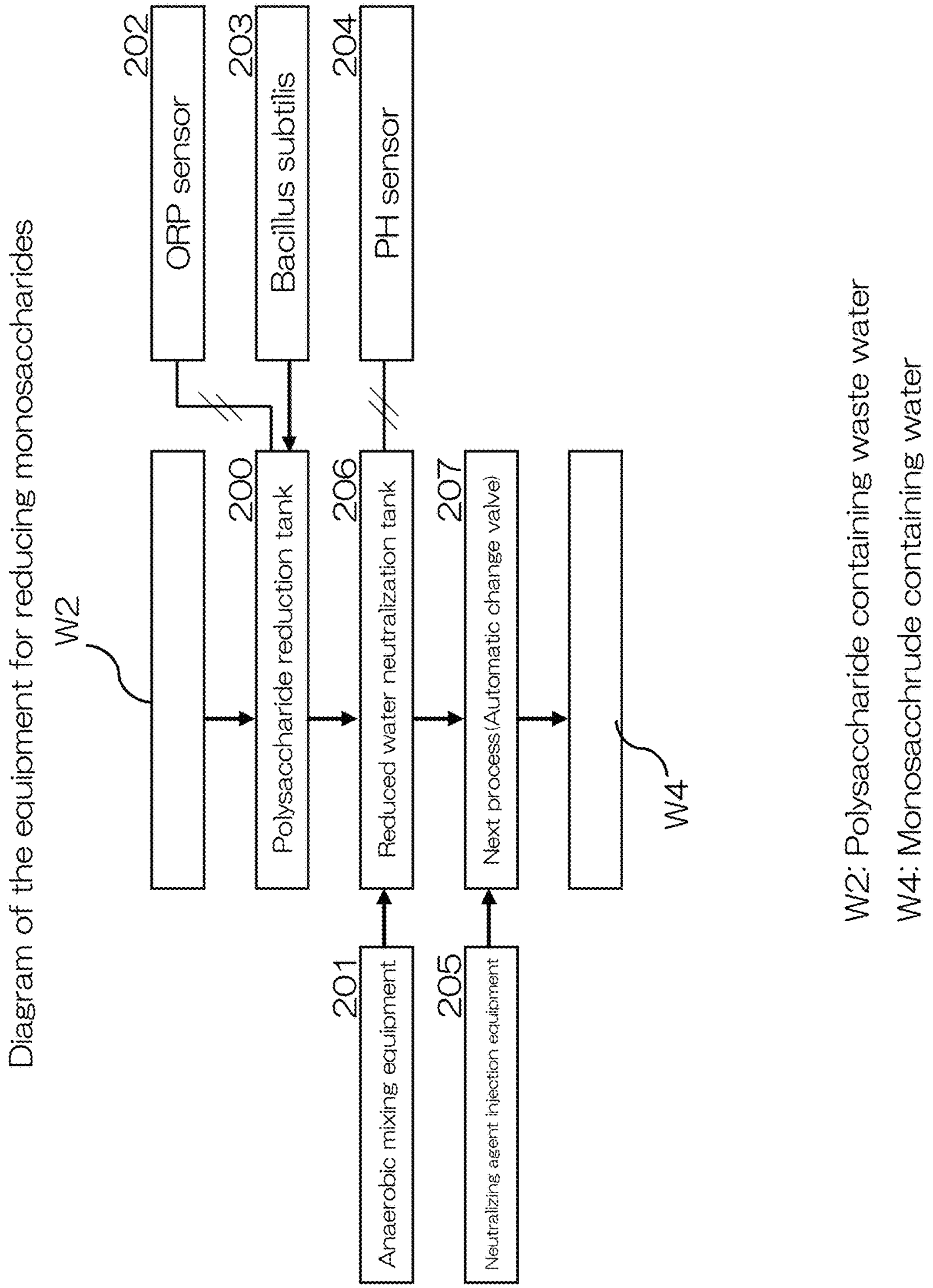
FIG. 8 it is a schematic view of a facility for carrying out the second polysaccharide reducing to monosaccharide step B) of the wastewater treatment method according to the present invention.
Figure 9:
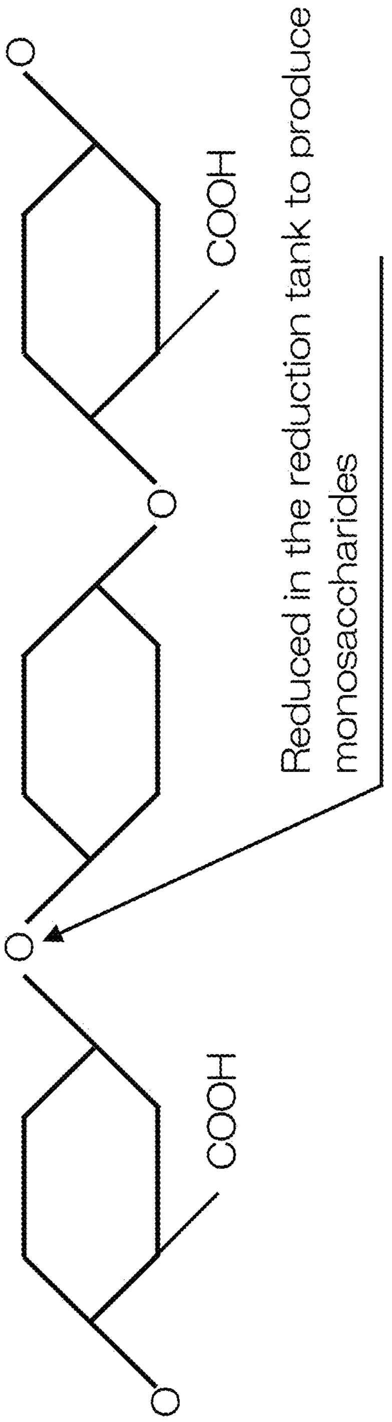
FIG. 9 it is an explanatory view showing the monosaccharide reducing reaction of the thickening polysaccharide in the second step B) of the wastewater treatment method of the present invention.

Then, the waste water whose BOD content has been adjusted is sent from the raw water adjusting tank 104 to the oil dispersing tank 106 via PID flow rate adjusting facility 104-2, from which the waste water is sent to the chemical-free pressurizing and surfacing facility 100, and the oil content in the waste water is pressurized and floated or levitated. Known pressurized flotation equipment can be used. Here, as shown in FIG. 7, the pressurized flotation facility 100 includes a pressurized flotation tank 100-1, from which the waste water is sent to the treated water pressurization pump 100-4, and the pressurized water and the pressurized air from the pressure regulating facility 100-3 controlled by the treated water pressurization conveyor 100-2 are mixed in the air melting tank 100-5 to obtain a separated floated oil containing wastewater W1. In this case, it is important to remove the oil content in the waste water containing the oil content and to make it anaerobic treatable water, and it is important to reduce the oil content in the waste water to a 100 ppm or less, preferably to a 30 ppm or less. The pressurized and floated oil waste water W1 is sent to the oil dispersing tank 106, while the remaining oil removing treated water W2 is sent to the thickening polysaccharide reducing tank 200. In the oil dispersing tank 106, the oil dispersing agent 107 is added, stirred, and emulsified. As the oil dispersant, a surfactant is used, but other equivalent oil dispersants can be used. Since it is important to make the separated and floated oil containing wastewater W1 to be aerobic treatable by emulsification, the following points should be taken into consideration.

Note: The raw water W is subjected to a, measurement by n-hexane Extraction Spectrometry (JIS) and adjusted to 500 ppm or less and then 80% of the oil content is removed so as to be 100 ppm or less, preferably 30 ppm or less. It is important that the oil content is in the form of emulsified wastewater of 0.5 μm or less.

3) (Single Saccharification Process of Oil-Removing Water W2)

Although the oil-removing water W2 obtained by separating the oil by the above-mentioned chemical-free pressurized flotation treatment contains some oil, the anaerobic treatment of the thickened polysaccharide is performed by *Bacillus subtilis* 203, so that the pretreatment makes it suitable for the activated sludge treatment. Other anaerobes existing in the air may be used instead of *Bacillus subtilis.*

There are increasingly used with polysaccharides such as isomerized sugars, dextrin with a low absorption rate in the body, polysaccharide pectin, gum syrup and the like. When polysaccharides are mixed into an aerobic biological treatment tank, the polysaccharide is denatured into a thickened polysaccharide by secretions (floc preparation glue, etc.) and oxygen (atoms) generated from the sludge, and the sludge is covered with a thickening substance, and the sludge inside becomes hypoxic, resulting in the inability to biodegrade. In addition, the sludge inside becomes anaerobic due to the lack of oxygen, and it takes 2 to 4 weeks to recover. In the sedimentation tank, it is difficult to perform solid-liquid separation (sedimentation separation) due to its viscosity, and it becomes a bulking state. Therefore, countermeasures against polysaccharides are essential, but the mechanism has not been academically elucidated. This was made possible by the monosaccharide treatment of the present invention. Although it is an estimation theory according to the experience of the present inventors, it is a valuable knowledge that the generation of viscosity can be suppressed by the monosaccharide treatment shown in FIG. 9.

In carrying out the anaerobic reducing monosaccharide treatment of the present invention, it is preferable to pay attention to the following points.

Notes:

In the monosaccharide treatment, not only the waste water in the reduction tank 200 is stirred in the anaerobic agitation facility 201 under anaerobic atmospheric conditions, but also the oxidation-reduction potential in the reduction tank 200 is measured by ORP sensor 202 to confirm whether or not the monosaccharide treatment of the thickened polysaccharide is completed. The treated water which became acid by the monosaccharide treatment is measured by PH sensors 204, and neutralized by injecting a neutralizing agent for example, NaOH from the neutralizing agent injection facility 205.

4) (Aerobic Biological Pretreatment Process)

Figure 10:
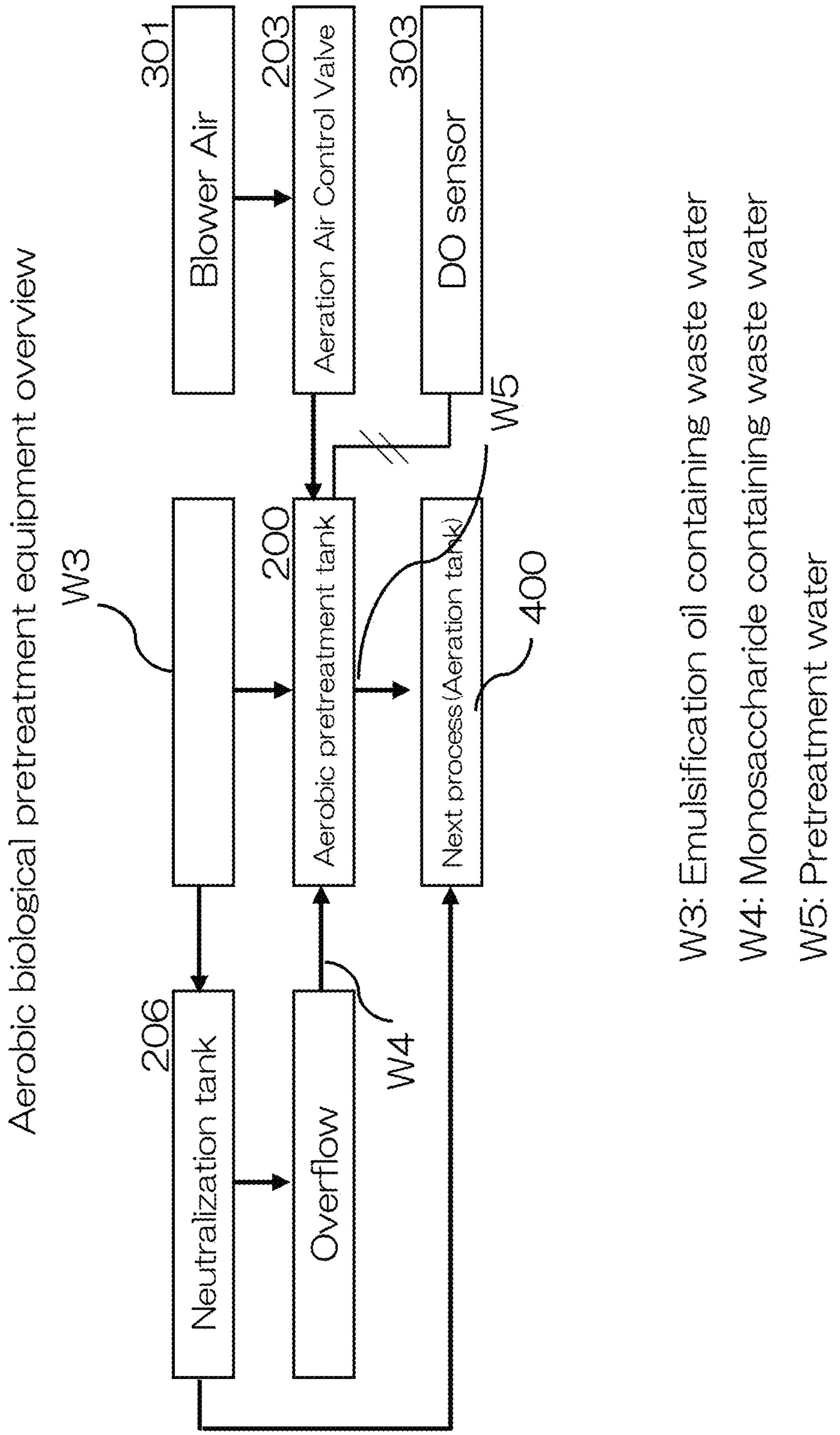
FIG. 10 it is a schematic view of a facility showing the third aerobic organism pretreatment step C) of the wastewater treatment method according to the present invention.

Here, as shown in FIG. 10, since the oil-dispersed waste water W3 obtained by emulsifying the separated floating oil waste water W1 and the reduced neutralized water W4 obtained by neutralizing after the reducing monosaccharide treatment become aerobic bacteria treatable water, these are treated with aerobic bacteria in the aerobic organism pretreatment tank 300 to obtain a pretreatment water W5 capable of aeration treatment. The aerobic biological pretreatment tank 300 is blown while measuring the oxygen demand by DO sensor 303 and while the blower air 301 is controlled by an aeration air control valve.

On the basis of the finding that the oil content and the thickening polysaccharide cannot be biotreated under the same conditions at the same time, it is very meaningful to divide the oil and thickening polysaccharide containing wastewater W into a waste water W1 containing the oil and a waste water W2 containing the thickening polysaccharide, and preferably to emulsify the former W1 into an aerobic biotreatable oil-dispersed waste water W3, while the latter W2 is reduced to monosaccharide and neutralized to a reduced neutralized water W4 capable of aerobic biotreatment, so that both of them can be used as a subsequent aerated water W5 by aerobic biotreatment.

Notes: such a pretreatment step should be performed considering the following points.

The first is the biological treatment using marine bacteria under aerobic conditions. Marine bacteria live widely in the ocean and are one of the microorganisms responsible for the natural purification system. Among them, Torula yeast is one of them, a very small, dispersible bacterium of a size that is only visible under a microscope of 2,000 times, and does not produce flocs different from standard activated sludge. The present applicant has been cultivating the marine bacteria in fresh water and desalinating them, and therefore according to the present invention, the marine bacteria combined with the subsequent activated sludge treatment becomes resulted in a wide range of industrial wastewater treatment. The functions of such marine bacteria are shown in FIG. 4. The present inventor has found that the above-mentioned reduced neutralized water W4 can be treated by such marine bacteria, so that the wastewaters W1 or W3 and W4 are simultaneously treated in the present pretreatment step.

Second, in such a pretreatment step, appropriate aerobic conditions need to be maintained while being measured by DO sensor—303. An aeration air control valve 302 controls the amount of blower air to be injected. As a result, it becomes a pretreatment water W5 that can be subjected to aeration treatment in the subsequent stage (D).

5) (Aeration-Sedimentation Process)

Figure 11:
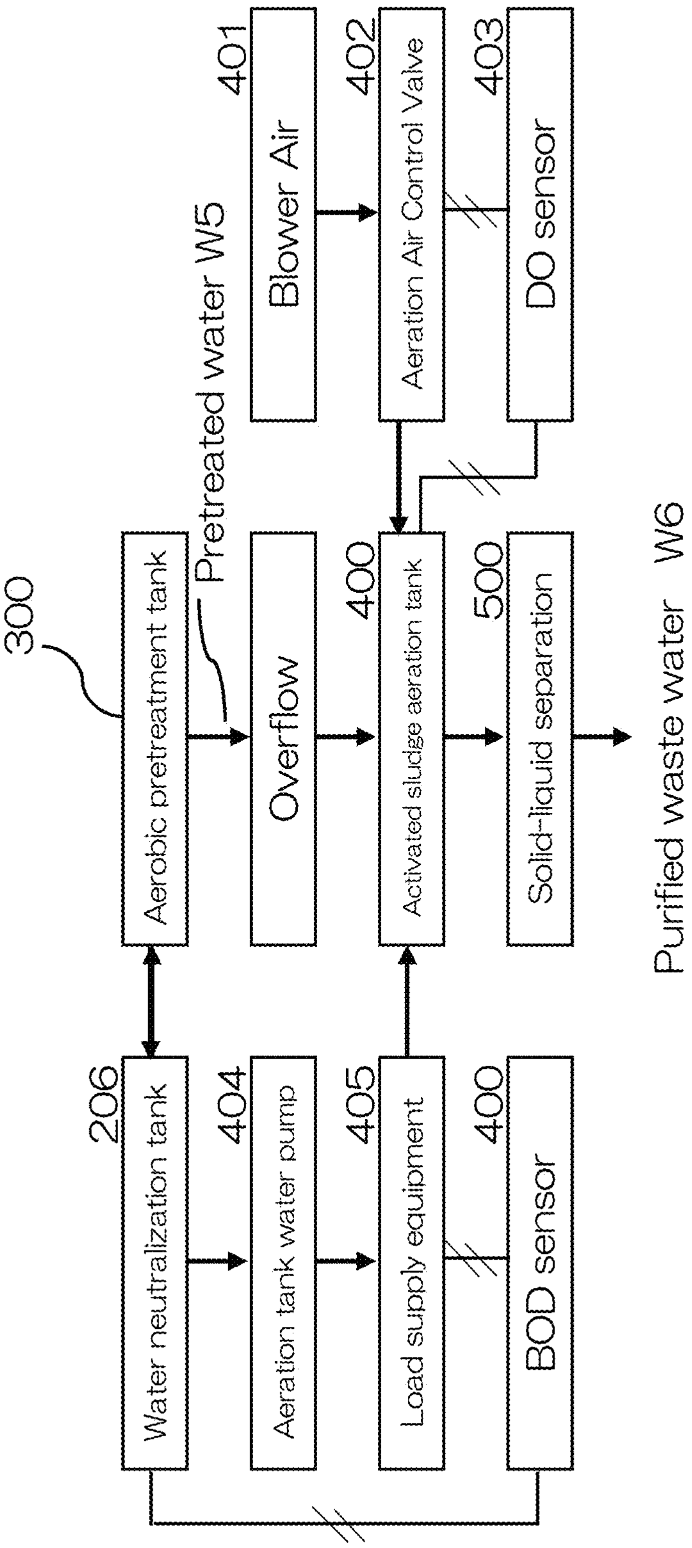
FIG. 11 it is a process flow diagram showing the fourth aeration solid-liquid separation step D) of the wastewater treatment method according to the present invention.

As shown in FIG. 11, the pretreated water W5 can be aerated while controlling BOD level, flocked with activated sludge, separated into solid and liquid, and discharged as purified wastewater.

In the step D), in aeration treatment of the pretreated wastewater W5 treated in the step C), as the noted points, it is essential to adjust the activated sludge to an appropriate loading by the reduced neutralized water W4 treated in the step B).

EXAMPLES

The wastewater containing the following oils and thickened polysaccharides was treated with activated sludge along the wastewater treatment system shown in FIG. 1 to obtain purified wastewater.

1) BOD concentration in wastewater W: Here, the wastewater to be treated contains oils and thickened polysaccharides, so that BOD concentration is adjusted to 1500-3000 and sent to a pressurized flotation tank.

2) Remove oils in the pressurized flotation tank and reduce the oil content in the remaining wastewater W2 to 100 ppm or less.

3) The wastewater W2 containing thickened polysaccharides is treated anaerobically with *Bacillus subtilis* for 4-24 hours in an anaerobic atmosphere at room temperature. The completion of the monosaccharide process was sensed by a ORP sensor, and NaOH was used as a neutralizing agent, and the completion of the neutralization process was managed by a PH sensor.

4) The oil dispersant 107 (e.g., surfactant) is added to the separated floating oil drainage W1 floated and collected in the pressurized flotation tank 100-1 with 1 to 20 mg/liter to the drainage, and is emulsified by stirring.

5) In the aerobic biological pretreatment, a predetermined amount of air is sent while the oxygen demand is detected by a DO sensor. Treatment is performed in an aerobic atmosphere at room temperature for 4 to 24 hours. Trula yeast is used as a marine bacterium, and the organic matter in the wastewater that is monosaccharide is used as a feed. Torula yeast will decompose (reduce the molecular weight) the oil content in the wastewater and make it an aeration-treatable water.

6) In the aeration process, DO sensor detects the oxygen demand, and the aeration process is performed at room temperature for 10 to 24 hours.

7) In the sedimentation tank, the flocked organic matter is solid-liquid separated. BOD level in the purified wastewater W6 decreases from 1/10 to 1/100 of the inflow wastewater W. Purified wastewater W6 is stored in the discharge monitoring water tank 600, and discharged sequentially while being monitored by the discharge water monitoring meter 601.

EXPLANATION OF REFERENCE NUMERALS

100 . . . pressurized flotation equipment
200 . . . thickening polysaccharide reducing tank
300 . . . aerobic biological pretreatment tank

What is claimed is:

1. A method for biotreating a persistent organic wastewater W containing an oil content containing fatty acids and a thickening polysaccharide, comprising: A) subjecting a waste water W to an oil-water separating process to separate it into an aerobically treatable oil-containing waste water W1 and an anaerobically treatable polysaccharide-containing waste water W2, B) subjecting the anaerobically treatable polysaccharide-containing waste water W2 to a reducing process in an anaerobic treatment to convert the polysaccharide in the waste water W2 into a monosaccharide and to obtain a monosaccharide water W4 capable of aerobic treatment, C) subjecting the oil-containing waste water W1 and the monosaccharide containing water W4 to an aerobic bacteria treatment process into a pretreatment water W5 capable of aeration treatment, and D) subjecting the pretreatment water W5 capable of aeration treatment to an aeration treatment process while controlling BOD density, and also subjecting it to a solid-liquid separation by flocculating with activated sludge.

2. The method for biotreating a persistent organic wastewater W containing an oil content containing fatty acids and a thickening polysaccharide according to claim 1, wherein: the step B) for reduction of the polysaccharide-containing waste water W2 by anaerobic treatment is performed by anaerobic treatment with *Bacillus subtilis* or anaerobic bacteria existing in air and the resulting wastewater is subjected to a neutralization.

3. The method for biotreating persistent organic wastewater W containing an oil content containing a fatty acid and a thickening polysaccharide according to claim 1, wherein: the oil-water separation step A) comprises an emulsifying process by addition of an oil dispersant and a pressurized process for separating the wastewater W into an oil-containing waste water W1 polysaccharide-containing waste water W2 in order to form an emulsified oil-containing water W3.

4. The method for biotreating persistent organic wastewater W containing an oil content containing a fatty acid and a thickening polysaccharide according to claim 1, wherein: in the process C), the oil-containing wastewater W1 separated in the process A) or the emulsified water treatment W3 thereof, and the monosaccharide-treated water W4 reduced in the process B) are treated using marine bacterium, including Tolla yeast.

5. The method for biotreating persistent organic wastewater W containing oil content containing a fatty acid and a thickening polysaccharide according to claim 4, wherein, in the step D), the pretreatment wastewater W5 treated in the step C) is aerated, the wastewater treatment process is performed by adjusting the wastewater W4 treated in the step B) to an appropriate BOD content of the activated sludge.

* * * * *